(12) United States Patent
Tower

(10) Patent No.: US 7,524,302 B2
(45) Date of Patent: Apr. 28, 2009

(54) PRENATAL BALLOON CATHETER

(75) Inventor: Allen J. Tower, North Lawrence, NY (US)

(73) Assignee: Numed, Inc., Nicholville, NY (US)

( * ) Notice: Subject to any disclaimer, the term of this patent is extended or adjusted under 35 U.S.C. 154(b) by 609 days.

(21) Appl. No.: 10/738,659

(22) Filed: Dec. 17, 2003

(65) Prior Publication Data
US 2005/0148880 A1    Jul. 7, 2005

(51) Int. Cl.
*A61M 29/00* (2006.01)
(52) U.S. Cl. ..................... 604/96.01; 604/192
(58) Field of Classification Search .............. 604/96.01, 604/103.05, 915, 103.03, 164.01, 264, 272; 600/470, 459; 606/192, 198
See application file for complete search history.

(56) References Cited

U.S. PATENT DOCUMENTS

| | | | |
|---|---|---|---|
| 4,582,061 A | 4/1986 | Fry | |
| 4,913,701 A | 4/1990 | Tower | |
| 4,946,440 A | 8/1990 | Hall | |
| 5,370,134 A | * 12/1994 | Chin et al. | 128/898 |
| 6,120,437 A | * 9/2000 | Yoon et al. | 600/204 |
| 6,436,088 B2 | 8/2002 | Frazier et al. | |
| 6,458,100 B2 | 10/2002 | Roue et al. | |
| 2003/0105410 A1 | 6/2003 | Pearlman | |

FOREIGN PATENT DOCUMENTS

| | | |
|---|---|---|
| EP | 0 624 342 A1 | 11/1994 |
| WO | 98/19713 | 5/1998 |

\* cited by examiner

*Primary Examiner*—Nicholas D Lucchesi
*Assistant Examiner*—Christopher D Koharski
(74) *Attorney, Agent, or Firm*—Hiscock & Barclay, LLP; R. Stephen Rosenholm

(57) ABSTRACT

A hollow metallic needle for guiding a balloon catheter into a fetal vessel or cavity. The needle initially contains a removable obturator which is removed after the needle is generally positioned within the fetus and is replaced by a balloon catheter. A plastic sleeve is mounted upon the distal end of the needle and sufficient air is entrapped within pockets formed in the sleeve to provide an enhanced ultrasonic image return so that a more accurate placement of the balloon is obtainable. The plastic sleeve extends beyond the distal end of the needle and serves to guide the balloon when deflated back into the needle and thus protects the balloon from snagging upon the edge of the needle.

5 Claims, 1 Drawing Sheet

PRENATAL BALLOON CATHETER

FIELD OF THE INVENTION

This invention relates to ultrasonic imaging and in particular to an enhanced ultrasonic imaging technique that is especially beneficial when positioning a balloon catheter within an unborn fetus.

BACKGROUND OF THE INVENTION

Ultrasonic imaging is widely used in the medical field because its non-ionizing radiation present a low risk to the patient being treated. The ultrasonic devices that have been developed employ sound frequencies in the 1 to 20 MHz range. Pulses within this range are propagated through the body of a patient and a small portion of the energy is reflected back to provide an image of the tissue upon which the sound waves have impinged with the brightness of reflected signal being a measure of tissue density. Doppler shifting of the returning sound can also be used to determine the flow velocity of moving structures such as blood moving through a vessel or an organ.

Ultrasonic instruments are widely-used to study the functioning of an unborn fetus as well as diagnosing disorders that might be present within the fetus. One such disorder is a malfunction of the aortic valve. If not timely treated while the fetus is into womb, the baby will invariable not be alive at birth. The accepted practice for treating this type of malfunction is to insert a balloon catheter into the troubled area and inflating and deflating the balloon to assist the heart and the aortic valve in establishing a rhythmic beat.

The balloon is positioned within the aorta using a needle that includes a thin walled tubular body and an obturator that is removably contained within the body section. The needle is passed into the fetus through the abdominal wall of the mother and then into the aorta. Once the needle is generally positioned, the obturator is removed and a balloon, which is attached to the distal end of a catheter is passed through the needle and is more accurately located within the aorta. Here again, ultrasonic imaging is employed to position the needle and thus locate the balloon within the aorta in order to protect both the mother and the baby from harm during the procedure.

Although ultrasonics at the 1-10 MHz range provides a relatively good image of human tissue, the return from metal objects is considerably less than satisfactory. Accordingly, accurate positioning of a metal needle within a fetus is difficult to arrive at and sometimes involves a good deal of guess work on the part of the attending physician. It is also sometimes rather difficult to withdraw the catheter through the needle at the end of the procedure because the deflated balloon can become snagged by the tip of the thin walled needle as the deflated balloon re-enters the body section. In some cases the balloon can be stripped from the catheter worsening the re-entry problem.

SUMMARY OF THE INVENTION

It is an object of the invention to improve procedures for positioning a metallic article within a human body using an ultrasonic imager.

A still further object of the present invention is to more accurately position a balloon catheter within a vessel or cavity of an unborn fetus.

Another object of the present invention is to better facitate the removal of a deflated balloon from a vessel or cavity of an unborn fetus.

Yet another object of the present invention is to prevent a deflated balloon that is mounted upon a catheter from snagged upon the tip of a thin walled delivery needle as the catheter is being withdrawn from a fetal vessel or cavity.

These and other objects of the present invention are attained in a delivery system for positioning a balloon catheter within a vessel of an unborn fetus that resides within the mothers womb. The delivery system includes a needle that includes a thin walled tubular body section containing a removable obturator. The needle is passed through the mothers abdominal wall into the fetus and is positioned within a desired fetal vessel or cavity using ultrasonic imaging in order to protect both the mother and the baby. The obturator is then removed from the body section of the needle and a catheter containing a deflated balloon at its distal end is passed into the treatment region through the body section and the balloon is inflated to carry out a procedure for addressing a given malfunction. A plastic sleeve is placed over the needle so that air is trapped between the needle and the sleeve. The entrapped air provides a bright return under ultrasonic imaging whereby the needle can be accurately positioned within the vessel or cavity. The sleeve extends outwardly beyond the distal end of the body section and serves to provide a non-snagging contact surface for the deflated balloon as it is being withdrawn into the needle. The extended portion of the sleeve also serves to compact and guide the balloon into the distal end entrance to the body section thus preventing the balloon from becoming snagged during the withdrawal procedure.

BRIEF DESCRIPTION OF THE DRAWINGS

For a better understanding of these and other objects of the invention, reference will be made to the following detailed description of the invention that is to be read in association with the following drawings, wherein.

DETAILED DESCRIPTION OF THE INVENTION

Figure 1:
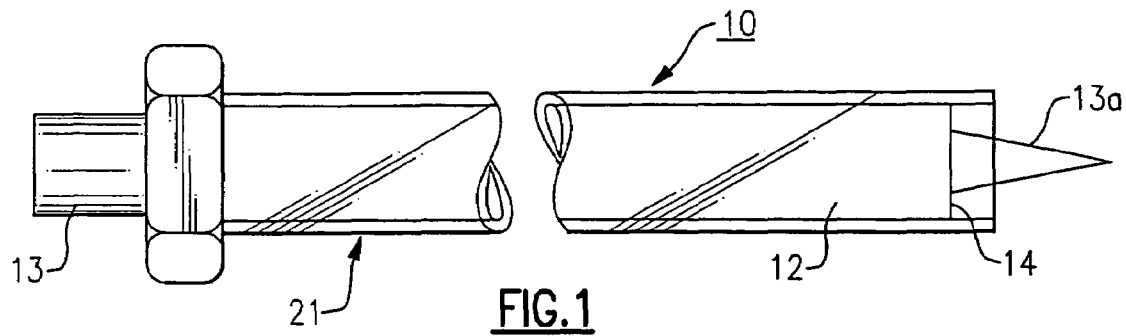
FIG. 1 is an enlarged side elevation of a needle obturator that is employed in the practice of the present invention.

Turning now to the drawings, there is illustrated in FIG. 1 a needle 10 that is employed to guide and position a balloon catheter within a fetal vessel or cavity such as the aorta or pulmonary artery of a fetus while the fetus is still in its mothers womb for purpose of addressing some type of diagnosed malfunction. The needle includes a thin walled tubular body section 12 that removably contains an obturator 13 that has a pointed distal end 13a that protrudes outwardly from the distal end 14 of the body section. Because needle rigidity is required for this type of procedure, the body section of the needle is constructed of metal such as a stainless steel tube or the like. The thin walled tubular body typically has an outside diameter of about 0.050 inches so that it can be inserted into small fetal vessels or cavities such as the aorta or the pulmonary artery. The pointed tip of the obturator provides a sharp edge that enables the needle to penetrate the abdominal wall of the mother and the tissue of the fetus while causing a minimal amount of tissue damage.

Figure 2:
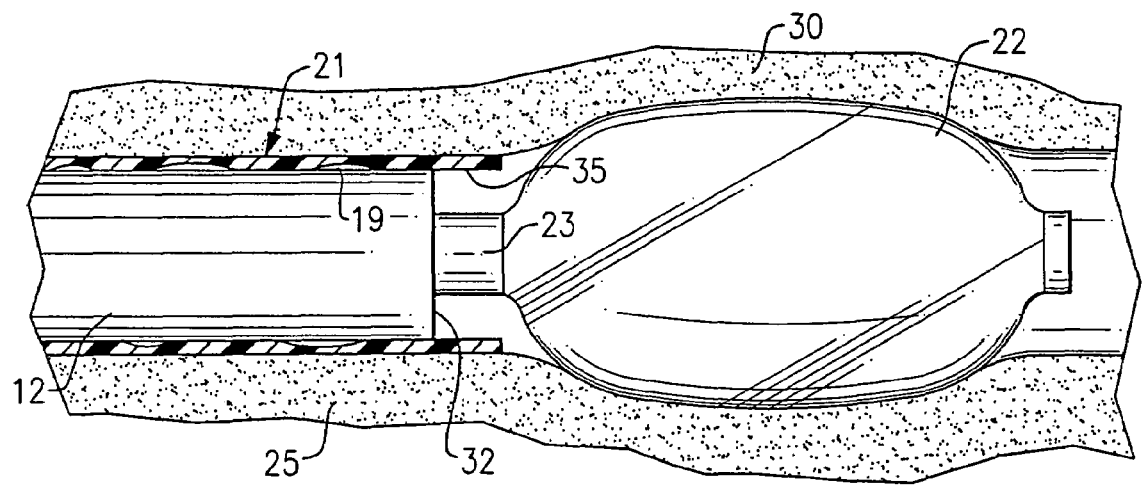
FIG. 2 is an enlarged side elevation showing the body section of the needle positioned within a fetal vessel and a balloon that is mounted upon a catheter inflated within the vessel.
Figure 3:
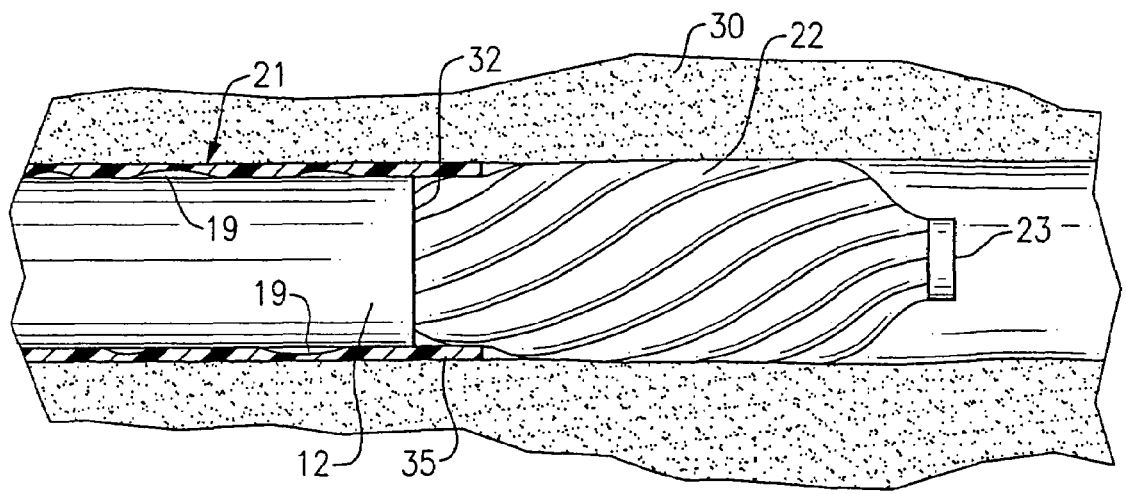
FIG. 3 is a further enlarged side elevation illustrating the balloon in a deflated condition as it is being drawn back into the body section of the needle.

As noted above, in order to protect both the mother and the fetus, the insertion and positioning of the needle within the fetal vessel is done with the aid of data provided by ultrasonic imaging equipment. Once the needle is located in a desired position, the obturator is removed from the needle body and a deflated balloon 22 that is mounted on the distal end of a catheter 23 is passed through the needle into the treatment region and inflated as illustrated in FIG. 2. As noted above, one such procedure involves positioning the balloon within the aorta of a fetus to assist the aortic valve and the heart to establish a rhythmic beat. At the end of the procedure, the balloon is deflated as illustrated in FIG. 3 and is withdrawn back into the needle body section to facilitate safe removal of the needle and catheter from the fetus and the mother.

One long standing problem that is associated with ultrasonic imaging used for medical purposes involves the relatively weak return that this type of imaging produces from metal articles, such as insertion needles. This weak return makes positioning of a needle extremely difficult. Particularly when attempting to position the needle within a fetal cavity or vessel, such as vessel 30 shown in FIGS. 2 and 3. Through experimentation, it has been discovered that by trapping air along at least a portion of the needles length the ultrasonic echo return from the needle is greatly enhanced thus taking away most of the guess work in positioning the needle within a fetus. To this end, the plastic sleeve 21 is fabricated of a heat shrinkable material and the sleeve is then placed over the needle and is shrink fitted to the needle body in an air atmosphere to trap pockets of air 19 between the sleeve and the body section of the needle. The sleeve is thus tightly fitted to the needle body so that it will not become dislodged when the needle is placed in use and the air that is entrained between the needle body and the sleeve can not escape to the surrounding ambient.

Although shrink fitting a plastic sleeve upon the needle body is one means of entrapping air along a length of the body any other method that is capable of similarly entrapping air can be used without departing from the practice of the present invention. It should also be noted, that the invention is not limited for use in association with insertion needle into a fetus and can be utilized in association with any type of article that gives a weak return echo under ultrasonic imaging to enhance the brightness of the return image.

Withdrawal of a deflated balloon 23 back into the thin walled needle body 12 during a prenatal procedure has also presented problems. The shape of the deflated balloon is often such that the balloon can snag or hang up upon the thin edge 32 at the distal end entrance to the tubular body section. In certain cases the snagged balloon or portions thereof can be dislodged from the catheter posing an additional problem. To alleviate this danger, one end of the sleeve that has been shrink fitted to the needle body is extended outwardly beyond the distal edge 32 of the needle body to provide a relatively soft and pliable guideway 35 for engaging and guiding the collapsed balloon into the distal end entrance as the catheter is being withdrawn into the body section. Typically the balloon is fabricated of nylon or a similar material which can slide easily over the surface of the sleeve without the danger of catching or snagging on the sleeve. In addition to guiding the deflated balloon into the body entrance, the sleeve also serves to contour or shape the balloon into a compact package that will pass freely through the entrance region of the body section.

While the present invention has been particularly shown and described with reference to the preferred mode as illustrated in the drawing, it will be understood by one skilled in the art that various changes in detail may be effected therein without departing from the spirit and scope of the invention as defined by the claims.

I claim:

1. An apparatus for accurately positioning a needle within a ultrasonic field that includes:
   a thin metal hollow needle;
   a catheter having an inflatable balloon affixed to its distal end that is slidably contained within said needle and whereby said balloon can be passed through and out of said needle;
   a plastic sleeve that is rigidly affixed to said needle so that said sleeve moves in unison with said needle;
   one or more pockets that entrap air between said plastic sleeve and a wall of said needle, each of said pockets being disposed at fixed locations along said wall of said needle, said fixed locations being located in between areas of surface contact between said plastic sleeve and said wall of said needle, so that each of said pockets move in a fixed relationship with movement of said needle.

2. The apparatus in claim 1 wherein said sleeve is fabricated of a heat shrinkable material that is securely shrink fitted around the outer surface of said needle.

3. The apparatus of claim 2 wherein the distal end of said sleeve extends outwardly beyond the distal end of said needle sufficiently to guide said balloon after deflation back into said needle and prevent snagging of said deflated balloon upon the distal end of said needle as the deflated balloon is being withdrawn into said needle.

4. The apparatus of claim 2 wherein said pockets are located along the interior surface of said sleeve.

5. The apparatus of claim 4 wherein said pockets are cusp shaped and are arranged to close against the outer surface of said needle to entrap air therein when said sleeve is shrink fitted to said needle.

* * * * *